(12) United States Patent
Ma et al.

(10) Patent No.: US 11,413,430 B2
(45) Date of Patent: Aug. 16, 2022

(54) NEEDLE MAGNETIZER

(71) Applicant: Becton, Dickinson and Company, Franklin Lakes, NJ (US)

(72) Inventors: Yiping Ma, Layton, UT (US); S. Ray Isaacson, Layton, UT (US); Jonathan Karl Burkholz, Salt Lake City, UT (US); Brian Jensen, Orem, UT (US); Daniel Robinaugh, Orem, UT (US); Derek Sanchez, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 16/943,162

(22) Filed: Jul. 30, 2020

(65) Prior Publication Data
US 2020/0360662 A1 Nov. 19, 2020

Related U.S. Application Data

(62) Division of application No. 15/944,324, filed on Apr. 3, 2018, now Pat. No. 10,765,835.
(Continued)

(51) Int. Cl.
*A61M 25/01* (2006.01)
*A61M 25/06* (2006.01)
(Continued)

(52) U.S. Cl.
CPC ........ *A61M 25/0127* (2013.01); *A61M 5/427* (2013.01); *A61M 25/0606* (2013.01);
(Continued)

(58) Field of Classification Search
CPC ............. A61M 25/0127; A61M 5/427; A61M 25/0618; A61M 25/0606;
(Continued)

(56) References Cited

U.S. PATENT DOCUMENTS

| 2,110,123 | A | 3/1938 | Eisele |
| 5,055,813 | A | 10/1991 | Johnson |

(Continued)

FOREIGN PATENT DOCUMENTS

| EP | 0281421 A2 | 9/1988 |
| JP | 2014529477 A | 11/2014 |

(Continued)

*Primary Examiner* — Theodore J Stigell
*Assistant Examiner* — Rachel T. Smith
(74) *Attorney, Agent, or Firm* — Servilla Whitney LLC

(57) ABSTRACT

A device for accommodating and magnetizing a tissue-penetrating medical device of various lengths, with or without a cover covering a portion or the entirety of the tissue-penetrating medical device, is disclosed including a sleeve member having an open proximal end, a distal end, an inner surface, an outer surface having a graduated injection depth gauge to indicate needle penetration depth when the cover is placed into a magnetizer, and a hollow body extending between the proximal end and the distal end to form a protective closure over a shaft of a tissue-penetrating medical device. A device having one or more magnetizing elements sectioned into a plurality of movable segments pivoting around an axis to accommodate needles with different lengths is also disclosed. Also disclosed is a device having one or more magnetizing means mounted on a movable element to magnetize needles of various lengths.

11 Claims, 5 Drawing Sheets

Related U.S. Application Data

(60) Provisional application No. 62/481,964, filed on Apr. 5, 2017.

(51) Int. Cl.
    *H01F 13/00*         (2006.01)
    *A61M 5/42*         (2006.01)

(52) U.S. Cl.
    CPC ....... *A61M 25/0618* (2013.01); *H01F 13/003* (2013.01); *A61M 2205/0272* (2013.01)

(58) Field of Classification Search
    CPC .. A61M 2205/0272; A61M 2025/0166; A61M 2037/0007; A61M 2205/6054; H01F 13/003; H01F 7/02
    See application file for complete search history.

(56) References Cited

U.S. PATENT DOCUMENTS

| | | |
|---|---|---|
| 5,085,647 A | 2/1992 | Henderson et al. |
| 5,098,403 A | 3/1992 | Sampson et al. |
| 6,569,115 B1 | 5/2003 | Barker et al. |
| 2004/0127859 A1 | 7/2004 | Ward |
| 2007/0016146 A1 | 1/2007 | Yang |
| 2014/0253270 A1* | 9/2014 | Nicholls ................ A61B 5/062 335/284 |

FOREIGN PATENT DOCUMENTS

| | | |
|---|---|---|
| WO | 0071186 A1 | 11/2000 |
| WO | 2009007718 A1 | 1/2009 |
| WO | 2013138555 A2 | 9/2013 |
| WO | 2017196733 A1 | 11/2017 |
| WO | 2017196736 A1 | 11/2017 |
| WO | 2018044826 A1 | 3/2018 |

\* cited by examiner

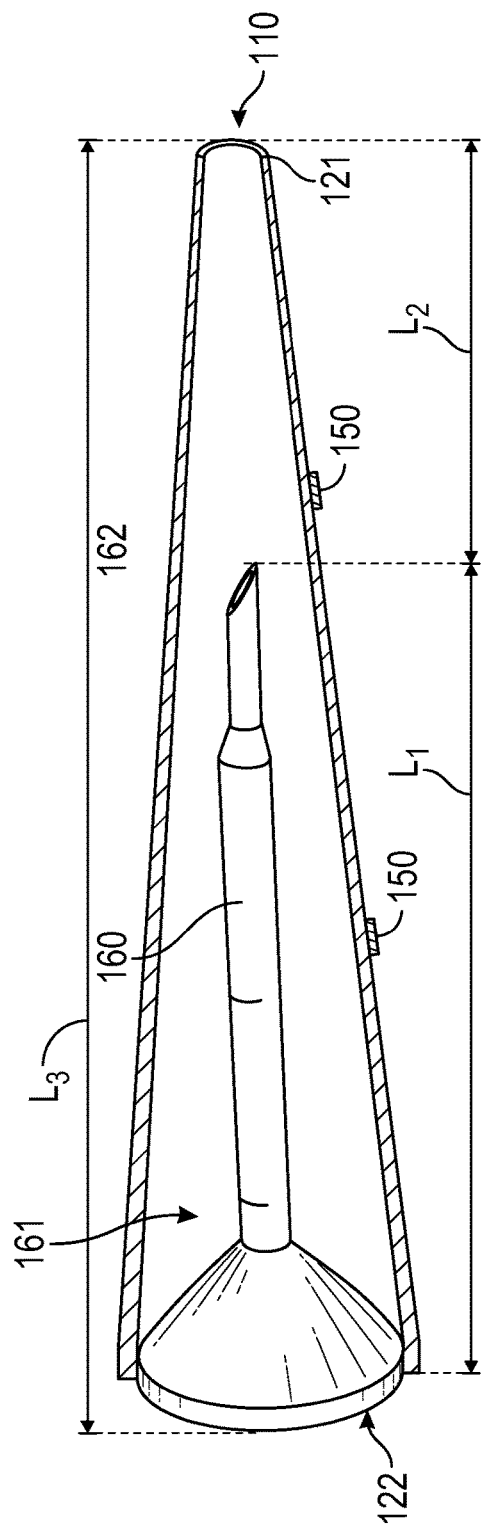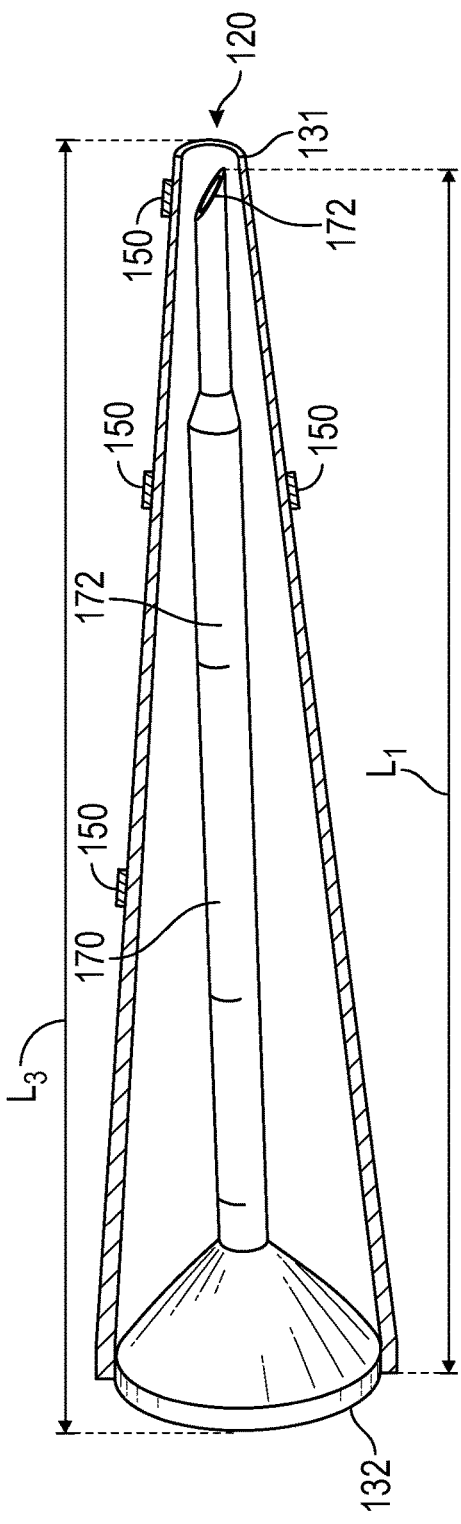
FIG. 2A
FIG. 2B

NEEDLE MAGNETIZER

CROSS-REFERENCE TO RELATED APPLICATIONS

This application is a divisional of U.S. patent application Ser. No. 15/944,324, filed on Apr. 3, 2018, which claims priority under 35 U.S.C. § 119(e) to U.S. Provisional Application No. 62/481,964, filed Apr. 5, 2017, the disclosures of which are incorporated herein by reference in their entirety.

BACKGROUND

Traditionally, penetration of an invasive medical device, such as a needle or catheter tubing, through skin tissue to reach the vein during needle or catheter insertion is invisible to clinicians. For this reason, clinicians must rely on their first-hand experience with needle insertion in combination with tactile sense to successfully identify the location of the vein. This may be a difficult task when attempting to access a small vein in a deep location under the skin, increasing risk of excess pain and/or injury to the patient. There are similar problems with insertion of other invasive medical devices such as guidewires, catheters, introducer needles, stylets, scalpels and guidewires with respect to the inability to precisely visualize the location of the invasive medical device.

Procedural guidance systems utilize a combination of ultrasound and magnetic technologies to provide visualization of subdermal anatomy and device position in the in-plane and out-of-plane orientations. Magnetized needles have been used to guide needle and catheter insertion in conjunction with ultrasound. This combination of ultrasound and magnetic methods also allows for the projection or anticipation of the insertion device position relative to the patient's anatomy, and thereby improves the likelihood of successfully accessing the vasculature and completing the invasive procedure.

The available technology today requires the clinician to manually magnetize the needle in a disposable magnetizer after the removal of the needle from a needle cover just prior to use. The use of needle cover while magnetizing the needle helps to eliminate the accidental damage to the needle tip while maintain the sterility of the device. However, the presence of the needle cover presents a dilemma where the clinicians could not see the needle tip or the length of the needle to be magnetized in most cases. This approach has the potential of resulting in needle tip damage, microbial contamination, and/or inconsistency in the length of magnetized section on the needle. Damage to the needle can occur that is not apparent to the user, which can negatively affect the insertion process. Also, active magnetization of a metal cannula by the user has some limitations and inherent risks, as this approach does not guarantee consistent magnetization since variability in clinician procedures such as depth of insertion, speed of process, and centering of the needle in the magnetizer will result in different degrees of magnetization. The section of the needle near the distal end to be magnetized is the same regardless of actual needle length. However, with a needle cover on the metal cannula, it is difficult for a practitioner to know where the needle is, given that standard needle covers are currently used to cover needles with various lengths. Thus, there is a need to provide visual confirmation to the practitioner for indicating needle penetration depth when the cover is placed into a magnetizer.

Considering the significant risk of needle tip damage, increased potential for contamination and inconsistent magnetization, it would be advantageous to have a system that consistently magnetizes the needle without introducing the aforementioned additional risks. In addition, it is costly to discard the magnetizer after each needle or catheter placement. Thus, there is a need for a device that ensures consistency in the length of the magnetized section of a needle or catheter either with or without a cover covering a portion or the entirety of the tissue-penetrating medical device.

SUMMARY

A first aspect of the disclosure pertains to a cover for magnetizing a tissue-penetrating medical device comprising a sleeve member having an open proximal end, a distal end, an inner surface, an outer surface, and a hollow body extending between the proximal end and the distal end. The sleeve member forms a protective closure over a shaft of a tissue-penetrating medical device having a longitudinal axis. The open proximal end of the sleeve member provides a receiving space for receiving at least the shaft of the tissue-penetrating medical device. The outer surface of the sleeve member has a graduated injection depth gauge to indicate needle penetration depth when the cover is placed into a magnetizer.

The graduated injection depth gauge can be printed, engraved, etched, embossed, or debossed onto an outer surface of the sleeve member. In one or more embodiments, the graduated injection depth gauge is scaled to correlate to a needle length.

In one or more embodiments, the cover is sterile. In one or more embodiments, the cover is disposable. In one or more embodiments, the cover can be plastic.

A second aspect of the disclosure pertains to a cover for magnetizing a tissue-penetrating medical device comprising an open proximal end, a distal end, and a cavity defining a device-receiving space. The cavity has an open proximal end and a distal tip to enclose a tissue-penetrating medical device. The cover has a first length $L_1$ between the open proximal end and the distal tip of the cavity. The cover has a second length $L_2$ between the distal tip of the cavity and the distal end. The cover has a third length $L_3$ between the open proximal end and the distal end.

In one or more embodiments, the first length $L_1$ is less than the third length $L_3$.

In one or more embodiments, the second length $L_2$ is less than the third length $L_3$.

In one or more embodiments, the third length $L_3$ is equal to the sum of the first $L_1$ and the second length $L_2$.

In one or more embodiments, the first length $L_1$ is the same as the third length $L_3$.

A third aspect of the disclosure pertains to a cover for magnetizing a tissue-penetrating medical device comprising a base segment having one or more magnets and a first central cavity, one or more movable segments having one or more magnets stacked in a vertical configuration on top of the base segment, the one or more segments having a second central cavity; and a hinge having a vertical axis not in contact with the first cavity and second cavity, the hinge connecting the one or more movable segments and the base segment. The movable segments can be rotatable, slidable or stackable.

In one or more embodiments, the first central cavity and the second central cavity permit movement of a tissue-penetrating medical device into the first central cavity and the second central cavity in a direction parallel to a longitudinal axis of the tissue-penetrating medical device.

In one or more embodiments, the first central cavity and the second central cavity permit movement of the shaft of the tissue-penetrating medical device into and out of the receiving space.

In one or more embodiments, there are two or more magnets disposed on the base segment. In one or more embodiments, there are two or more magnets disposed on each of the one or more movable segments. In one or more embodiments, the one or more magnets are a fixed permanent magnet.

A fourth aspect of the disclosure pertains to a magnetizer for magnetizing a tissue-penetrating medical device comprising an open proximal end, a distal end, a first sidewall, a first sliding element having one or more first magnets slidably connected to the first sidewall, a second sidewall, a second sliding element having one or more second magnets slidably engaged to the second sidewall, and a cavity formed between the first sidewall, second sidewall and distal end.

In one or more embodiments, the one or more first magnets are mounted on the first sliding element. In one or more embodiments, the one or more second magnets are mounted on the second sliding element.

In one or more embodiments, the first sliding element and/or second sliding element is movable in a parallel direction to an axis of the cavity.

In one or more embodiments, the first sliding element and/or second sliding element includes a contact surface having a profile for accommodating a practitioner's finger.

In one or more embodiments, the cavity is configured to accommodate a tissue-penetrating medical device.

In one or more embodiments, the tissue-penetrating medical device is a needle assembly, a stylet, catheter, introducer needle, scalpel or guidewire.

In one or more embodiments, the tissue-penetrating medical device includes a needle assembly including a needle and the shaft, and when the shaft is magnetized, the tissue-penetrating medical device is configured for use in a procedural guidance system to locate and project a position of the shaft during an invasive medical procedure.

In one or more embodiments, the cavity is configured to accommodate a needle cover.

In one or more embodiments, the one or more magnets comprise a fixed permanent magnet.

In one or more embodiments, the first sliding element is moveable along the first sidewall.

In one or more embodiments, the second sliding element is moveable along the second sidewall.

Another aspect of the present disclosure relates to a cover for magnetizing a tissue-penetrating medical device comprising a sleeve member having an open proximal end, a distal end, an inner surface, an outer surface, one or more physical stop elements disposed on the outer surface; and a hollow body extending between the proximal end and the distal end to form a protective closure over a shaft of a tissue-penetrating medical device. In one or more embodiments, the one or more physical stops correspond to different needle lengths to indicate needle penetration depth when the cover is placed into a magnetizer.

In one or more embodiments, the one or more physical stops correspond to different needle gauges to indicate needle penetration depth when the cover is placed into a magnetizer.

BRIEF DESCRIPTION OF THE DRAWINGS

FIG. 2A shows a perspective view of an alternate embodiment of a needle magnetizer of the present disclosure;

FIG. 2B shows a perspective view of an alternate embodiment of a needle magnetizer shown in FIG. 2A of the present disclosure;

DETAILED DESCRIPTION

Before describing several exemplary embodiments of the disclosure, it is to be understood that the description provided is not limited to the details of construction or process steps set forth in the following description. The devices and methods described herein are capable of other embodiments and of being practiced or being carried out in various ways.

In this disclosure, a convention is followed wherein the distal end of the device is the end closest to a patient and the proximal end of the device is the end away from the patient and closest to a practitioner.

Aspects of the disclosure pertain to an improved system that addresses the challenges to the existing technology and systems to magnetize a needle, such as a needle used with a peripheral intravenous (IV) catheter. Aspects of the disclosure pertain to an improved device and system that helps maintain the sterility of the tissue-penetrating device and also prevents damage to the distal tip of the tissue-penetrating medical device during magnetization of the tissue-penetrating medical device. Therefore, in one or more embodiments of the present disclosure, a tissue-penetrating medical device is magnetized with the cover of the present disclosure placed on the tissue-penetrating medical device. The section of the tissue-penetrating medical device, e.g. needle, near the distal end to be magnetized is the same regardless of actual needle length.

One or more embodiments of the present disclosure relate to a needle magnetizer that is capable of accommodating needles of various lengths with a cover of the present disclosure placed on the tissue-penetrating medical device. In an alternate embodiment of the present disclosure, a needle magnetizer is capable of accommodating needles of various lengths without a cover being placed on the tissue-penetrating medical device. According to one or more embodiments, the device and system of the present disclosure consistently magnetizes needles of various lengths with a cover of the present disclosure placed on the tissue-penetrating medical device. In one or more embodiments of the present disclosure, a tissue-penetrating medical device is magnetized without a cover placed on the tissue-penetrating medical device. In one or more embodiments, the devices and systems described herein provide more precise control of the location of the magnet relative to the device to be magnetized, resulting in a more consistent and predictable magnetic field applied to the invasive medical device. In one or more embodiments, the devices and methods described herein create no additional risk of needle damage compared to existing magnetizer devices and no additional risk for contamination compared to existing magnetizer devices. Rather, the devices, system and methods described herein reduce the risk of needle damage compared to existing magnetizer devices and reduce the risk for contamination compared to existing magnetizer devices.

Figure 1:
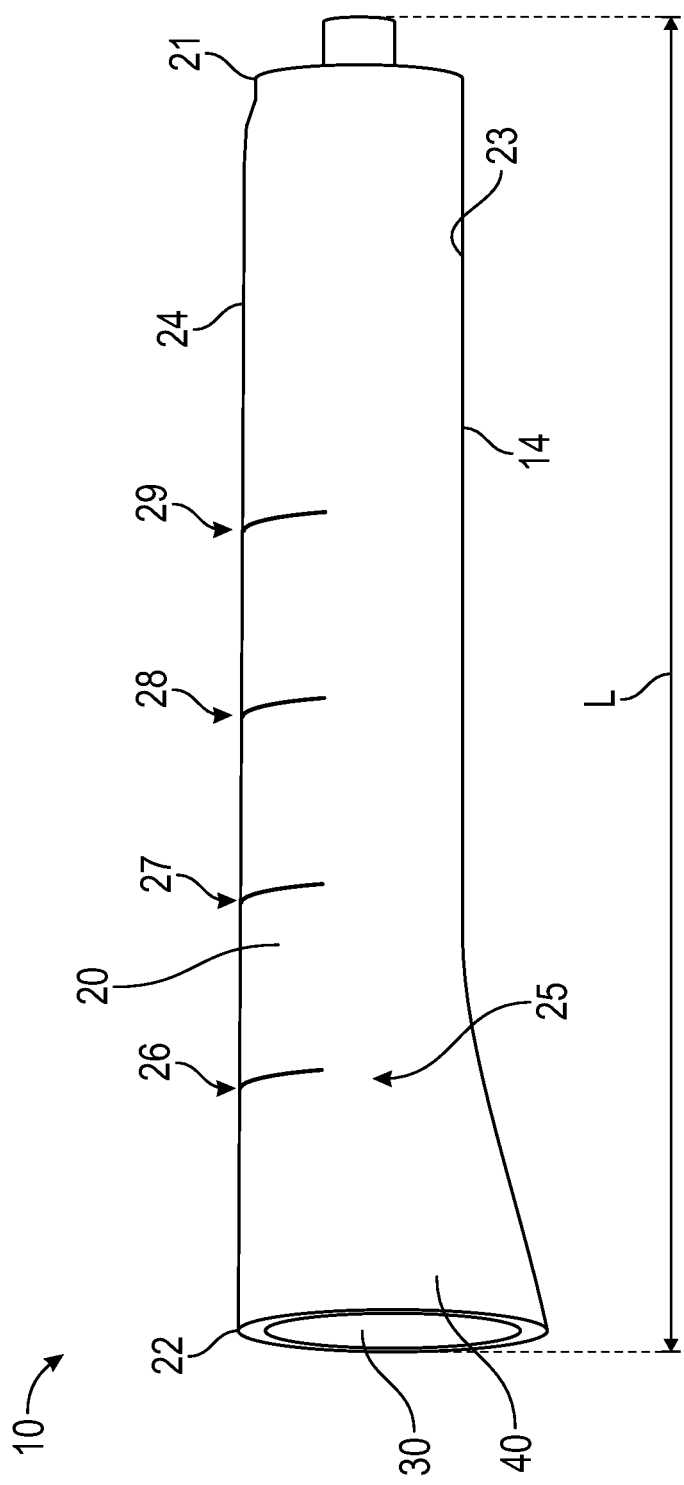
FIG. 1 shows a perspective view of an embodiment of a needle magnetizer of the present disclosure.

Referring now to FIG. 1, one aspect of the disclosure pertains to a cover 10 for a tissue-penetrating medical device, the cover having a sleeve member 14 having a hollow body 20 having a distal end 21, an open proximal end 22, an inner surface 23 and outer surface 24 to form a protective closure over a shaft of a tissue-penetrating medical device. In one or more embodiments, the hollow body 20 can be tubular or any other suitable shape.

In one or more embodiments, distal end 21 may be open. In one or more embodiments, distal end 21 may be closed.

Cover 10 can be used with tissue-penetrating medical devices, e.g. needles, with various lengths. As shown in FIG. 1, in one or more embodiments, the outer surface 24 of the sleeve member 14 includes a graduated injection depth gauge 25 having one or more lines (26, 27, 28, 29) to show how far to insert cover 10 into a magnetizer (not shown) for various desired lengths of needle magnetization. In one or more embodiments, multiple markings, e.g. lines (26, 27, 28, 29), can be placed on cover 10, whereby each marking corresponds to a different needle length to be used with cover 10. For example, in one or more embodiments, as shown in FIG. 1, if cover 10 is intended to cover tissue-penetrating medical devices having four (4) different lengths, there would be four (4) lines (26, 27, 28, 29) on the outer surface 24 of the sleeve member 14 of cover 10. The distance from the distal end of the tissue-penetrating medical devices, e.g. needle, to the marking for the given needle length is the same for all needle lengths with their corresponding markings, e.g. lines (26, 27, 28, 29). This way the length of needle tip section magnetized will be the same if the needle cover marking for the given needle length is aligned with a feature on a magnetizer. A tissue-penetrating medical device is placed into cover 10 via opening 30 of open proximal end 22. Cover 10 is then inserted into a magnetizer (not shown), and the user aligns lines (26, 27, 28, 29) of graduated injection depth gauge 25 to the desired intended length of needle magnetization. In one or more embodiments, lines (26, 27, 28, 29) of graduated injection depth gauge 25 provide visual confirmation to the user by indicating needle penetration depth when the cover is placed into a magnetizer.

In one or more embodiments, the graduated injection depth gauge 25 may be printed onto an outer surface 24 of the sleeve member 14. In another embodiment, the graduated injection depth gauge may be engraved, etched, embossed, debossed by molding or formed onto an outer surface 24 of the sleeve member 14 to assist the user in measuring the needle depth penetration. In one or more embodiments, the graduated injection depth gauge is scaled to correlate to a needle length.

Typically, manufacturers use the same needle cover for devices with different needle lengths and gauges. Therefore, the distances between the tips of the needle cover and the needle vary depending on the needle length and needle cover design. However, these distances are known to manufacturers and fixed for a given needle length and needle cover design. Therefore, a marking or graduated injection depth gauge on the needle cover that indicates the position of the needle tip or the desired length of the magnetized needle section would allow clinicians to insert the corrected length of the needle into the magnetizer, thus overcoming the shortcoming of the existing technology. Similarly, a needle cover design with same distance between needle tip and needle cover tip would achieve the same outcome.

A tissue-penetrating medical device can include a needle assembly including a needle housing and a shaft of the needle having a sharp distal tip. In one or more embodiments, the sleeve member 14 can be transparent to allow the shaft and needle cannula of a tissue-penetrating medical device to be visible. The sleeve member 14 has a length L that covers the shaft of the tissue-penetrating medical device, including the sharp distal tip to prevent accidental needle sticks. The arrows shown in FIG. 1 with respect to the length "L" also show the longitudinal axis of a needle shaft. The open end 22 of the hollow body 20 provides a device-receiving space 40 for receiving at least the shaft of the tissue-penetrating medical device.

The device-receiving space 40 is sized and shaped to permit movement of the shaft of the tissue-penetrating medical device into and out of the device-receiving space 40. In one embodiment, the device-receiving space 40 permits movement of the shaft of the tissue-penetrating medical device into the device-receiving space 40 in a movement that is parallel to the longitudinal axis of the shaft of tissue-penetrating medical device. The needle cannula magnetizes when the needle cannula, with cover 10, is inserted into a separate magnetizer (not shown). In an alternate embodiment, the needle cannula magnetizes when the needle cannula, without cover 10, is inserted into a separate magnetizer (not shown). The needle cannula magnetizes when the needle cannula, with cover 10, is inserted into a separate magnetizer (not shown). In one or more embodiments, a magnetizer consists of a cavity with at least one opening through which the needle can be inserted. The cavity and the opening are large enough to accommodate the tissue-penetrating medical device with its cover, thus ensuring the sterility and the integrity of the tissue-penetrating medical device. The cavity of the magnetizer can have openings on both ends to allow tissue-penetrating medical devices, with cover 10, of various lengths and widths to be inserted into the magnetizer to a desired depth for magnetization. In an alternate embodiment, the cavity of the magnetizer can have openings on both ends to allow tissue-penetrating medical device, without cover 10, of various lengths and widths to be inserted into the magnetizer to a desired depth for magnetization.

A magnetizer further consists of magnetizing means around the cavity such as permanent magnets or electromagnets, or other magnetizing means. A section of the tissue-penetrating medical device that is exposed to the magnetizing means is magnetized as the tissue-penetrating medical device is inserted and removed from the magnetizer.

In use, the user would insert the tissue-penetrating medical device with cover 10 into the magnetizer until the graduated injection depth gauge 25 on the outer surface 24 of sleeve member 14 is aligned with the top of the magnetizer. When the tissue-penetrating medical device is removed from the magnetizer, the desired section of the tissue-penetrating medical device, e.g. needle, would be magnetized. The graduated injection depth gauge 25 on the outer surface 24 of sleeve member 14 can be located at different locations along the outer surface 24 depending on the length and/or gauge of the tissue-penetrating medical device, e.g. needle. In one or more embodiments, cover 10 is sterile. In one or more embodiments, cover 10 is disposable. In one or more embodiments, cover 10 is plastic.

A second aspect of the present disclosure pertains to one or more tissue-penetrating medical device covers, such that the cover that can be used for tissue-penetrating medical device, e.g. needles, with different lengths. In one or more embodiments, each cover 110 or 120 is of a uniform length and is used with a tissue-penetrating medical device of variable lengths. One or more physical stop elements 150 are disposed on the outer surface of cover 110 or 120. In one or more embodiments, one or more physical stop elements 150 are molded onto the outer surface of cover 110 or 120. In one or more embodiments, the position of the physical stop elements 150 disposed on the outer surface of cover 110 or 120 correspond to different gauge or size of various tissue-penetrating medical devices to be used with cover 110 or 120. Therefore, the length or portion of the tissue-penetrating device that is magnetized when a user inserts cover 110 or 120 into a magnetizer until the physical stop elements 150 disposed on the outer surface of cover 110 or 120 that correspond to a desired gauge or size of the tissue-penetrating medical device reaches the top of the magnetizer. Therefore, the length or portion of the tissue-penetrating device that is magnetized is dependent on the length of the tissue-penetrating medical device within the cover 110 or 120. In one or more embodiments, one or more physical stop elements are disposed on the inner surface of a magnetizer. In one or more embodiments, the position of the physical stop elements 150 disposed on the inner surface of a magnetizer correspond to different gauge or size of various tissue-penetrating medical devices to be used with cover 110 or 120. Therefore, the length or portion of the tissue-penetrating device that is magnetized when a user inserts cover 110 or 120 into a magnetizer corresponds to the desired gauge or size of the tissue-penetrating medical device when the physical stop elements 150 disposed on the outer surface of cover 110 or 120 abuts the corresponding physical stop on the inner surface of a magnetizer.

As shown in FIG. 2A and FIG. 2B, a second aspect of the present disclosure, pertains to cover 110 and cover 120 which are designed to have a uniform fixed length between open proximal end (122, 132) and distal end (121, 131) of cover (110, 120) to enclose a tissue-penetrating medical device (160, 170). Therefore, the cover 110 or 120 is of a uniform length, which can accommodate a tissue-penetrating medical device of variable lengths, e.g. $L_1$ as shown in FIGS. 2A and 2B.

A tissue-penetrating medical device can include a needle assembly including a needle housing and a shaft of the needle having a sharp distal tip. The open proximal end 122 of cavity 161 provides a device-receiving space for receiving at least the shaft of the tissue-penetrating medical device (160, 170).

With respect to FIGS. 2A and 2B, length $L_1$ refers to the length between open proximal end (122, 132) of cover (110, 120) and the distal tip (162, 172) of a tissue penetrating medical device (160, 170).

Length $L_1$ represents the length to cover the shaft of a tissue-penetrating medical device, including the sharp distal tip to prevent accidental needle sticks. With respect to FIGS. 2A and 2B, length $L_2$ refers to the length between the distal tip (162, 172) of a tissue penetrating medical device (160, 170) to enclose a tissue-penetrating medical device and the distal end (121, 131) of cover (110, 120). In one or more embodiments, cover (110,120) can be tubular or any other suitable shape. With respect to FIGS. 2A and 2B, length $L_3$ refers to the length between the open proximal end (122, 132) of cover (110,120) and the distal end (121, 131) of cover (110, 120). In one or more embodiments, distal end (121, 131) may be open. In one or more embodiments, distal end (121, 131) may be closed. When a cover (110, 120) encloses a tissue-penetrating medical device (160, 170) and both are inserted into a magnetizer such that the distal end (121, 131) of cover (110, 120) contacts the bottom of a cavity of a magnetizer or physical stop elements 150 disposed on the outer surface of cover 110 or 120 that corresponds to desired gauge or size of the tissue-penetrating medical device reaches the corresponding physical stop on the inner surface of a magnetizer, a desired section of the tissue-penetrating medical device (160, 170) of length $L_1$ will be exposed to the magnetic field to be magnetized.

Cover (110, 120) is sized and shaped to permit movement of the shaft of the tissue-penetrating medical device (160, 170) into and out of the device-receiving space. In one embodiment, cover (110, 120) permits movement of the shaft of the tissue-penetrating medical device (160, 170) into the cover (110, 120) in a movement that is parallel to the longitudinal axis of the shaft of tissue-penetrating medical device. A metal portion of the tissue penetrating medical device (160, 170) magnetizes when the tissue penetrating medical device (160, 170), when cover (110,120) is inserted into a separate magnetizer. In an alternate embodiment, the metal portion of the tissue-penetrating medical device magnetizes when the tissue-penetrating medical device, without cover (110,120) is inserted into a separate magnetizer. The magnetizer consists of a cavity with at least one opening through which the cover (110, 120) can be inserted. The cavity and the opening of the magnetizer are large enough to accommodate the tissue penetrating medical device (160, 170) with cover (110, 120) to ensure the sterility and the integrity of the tissue penetrating medical device (160, 170) and its distal tip (162, 172). The magnetizer can have openings on both ends to allow tissue-penetrating medical devices with various lengths and cover 110 of various length $L_3$ to be inserted to desired depth. In one or more embodiments, distal end (121, 131) is open. In one or more embodiments, distal end (121, 131) is closed.

The magnetizer further consists of magnetizing means around the cavity such as permanent magnets or electromagnets, or other magnetizing means. A section of the tissue penetrating medical device (160, 170) that is exposed to the magnetizing means is magnetized as the tissue penetrating medical device (160, 170) is inserted and removed from the magnetizer. The magnetizer can have openings on both ends to allow tissue penetrating medical devices (160, 170) with various length $L_1$ and cover 110 or cover 120 of various lengths $L_3$ to be inserted to desired depth.

In one or more embodiments, as shown in FIG. 2A, length $L_1$ is less than length $L_3$. In one or more embodiments, as shown in FIG. 2A, length $L_2$ is less than length $L_3$. In one or more embodiments, as shown in FIG. 2A, length $L_3$ is about the sum of $L_1$ and length $L_2$. In one or more embodiments, as shown in FIG. 2B, length $L_1$ is approximately the same as length $L_3$. In one or more embodiments, each of the physical stop elements 150 disposed on the outer surface of cover 110 or 120 that corresponds to corresponding $L_1$, $L_2$ or $L_3$ of a desired gauge or size of the tissue-penetrating medical device.

Figure 2C:
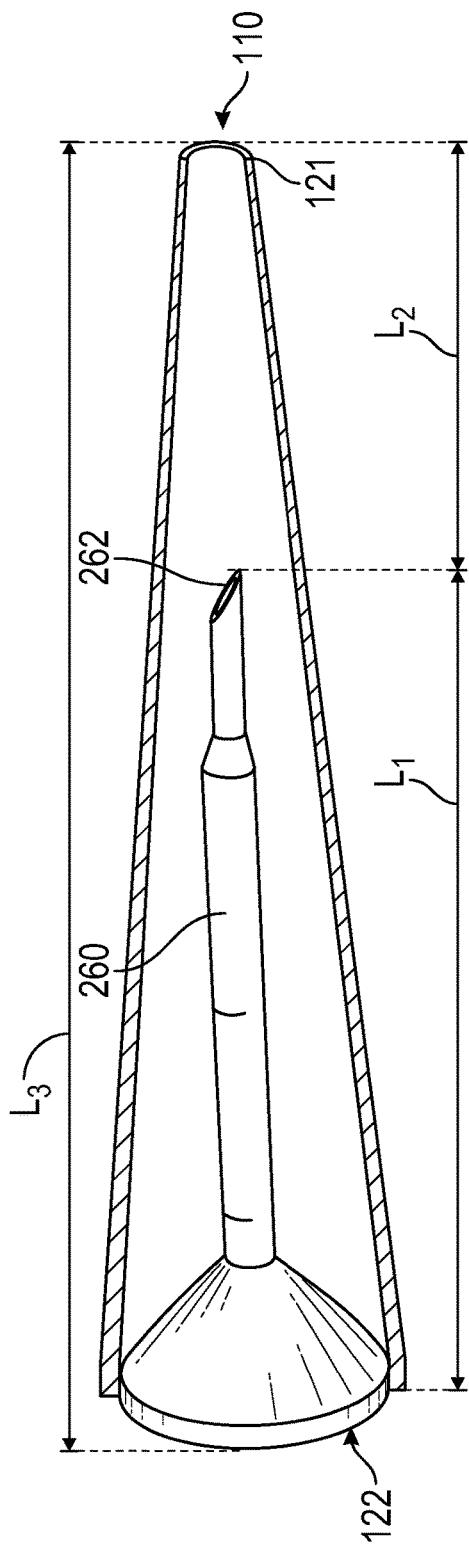
FIG. 2C shows a perspective view of an alternate embodiment of a needle magnetizer of the present disclosure.
Figure 2D:
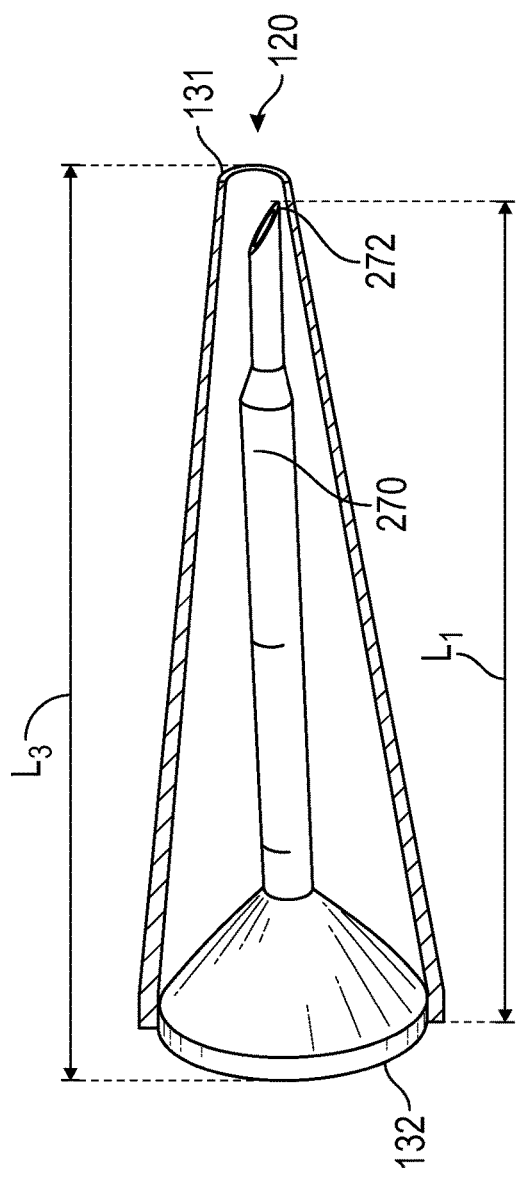
FIG. 2D shows a perspective view of an alternate embodiment of a needle magnetizer shown in FIG. 2C of the present disclosure.

As shown in FIG. 2C, in conjunction with FIG. 2D, an alternate embodiment, pertains to cover 110 and cover 120 which are designed to have different fixed lengths between the distal tip 162 of a cavity 161 to enclose a tissue-penetrating medical device and the distal end 121 of cover 110 or distal tip 131 of cover 120. Therefore, the cover 110 or 120 is used depending of the length of the tissue-penetrating medical device. Therefore, if the insertion depth of the tissue-penetrating medical device with cover into a magnetizer is the same, then the resulting length of the magnetized section of the tissue-penetrating medical device will also be the same for tissue-penetrating medical devices, e.g. needles, of different length.

With respect to FIG. 2C, length $L_1$ refers to the length between open proximal end 122 of cover 110 and the distal end 262 of a cavity 260 to enclose a tissue-penetrating medical device. In one or more embodiments, distal end 121 of cover 110 may be open. In one or more embodiments, distal end 121 of cover 110 may be closed.

A tissue-penetrating medical device can include a needle assembly including a needle housing and a shaft of the needle having a sharp distal tip. The open proximal end 122 of cavity 161 provides a device-receiving space for receiving at least the shaft of the tissue-penetrating medical device.

Length $L_1$ represents the length to cover the shaft of a tissue-penetrating medical device, including the sharp distal tip to prevent accidental needle sticks. With respect to FIG. 2C, length $L_2$ refers to the length between the distal end 262 of a cavity 161 to enclose a tissue-penetrating medical device and the distal end 121 of cover 110. In one or more embodiments, the cavity 260 can be tubular or any other suitable shape. With respect to FIG. 2C, length $L_3$ refers to the length between the open proximal end 122 of cover 110 and the distal end 121 of cover 110. When a cover 110 encloses a tissue-penetrating medical device and both are inserted into a magnetizer such that the distal end 121 of cover 110 contacts the bottom of a cavity of a magnetizer, a desired section of the tissue-penetrating medical device of length $L_1$ will be exposed to the magnetic field to be magnetized.

The cavity 260 is sized and shaped to permit movement of the shaft of the tissue-penetrating medical device into and out of the device-receiving space. In one embodiment, the cavity 260 permits movement of the shaft of the tissue-penetrating medical device into the cavity 260 in a movement that is parallel to the longitudinal axis of the shaft of tissue-penetrating medical device. A metal portion of the tissue-penetrating medical device magnetizes when the tissue-penetrating medical device, with cover 110, is inserted into a separate magnetizer. In an alternate embodiment, the metal portion of the tissue-penetrating medical device magnetizes when the tissue-penetrating medical device, without cover 110, is inserted into a separate magnetizer. The magnetizer consists of a cavity with at least one opening through which the needle can be inserted. The cavity and the opening of the magnetizer are large enough to accommodate the tissue-penetrating medical device with its cover thus ensures the sterility and the integrity of the needle. The magnetizer can have openings on both ends to allow tissue-penetrating medical devices with various lengths and cover 110 of various length $L_3$ to be inserted to desired depth.

The magnetizer further consists of magnetizing means around the cavity such as permanent magnets or electromagnets, or other magnetizing means. A section of the needle that is exposed to the magnetizing means is magnetized as the needle is removed from the magnetizer.

With respect to FIG. 2D, length $L_1$ refers to the length between open proximal end 132 of cover 120 and the distal tip 172 of a cavity 270 to enclose a tissue-penetrating medical device. A tissue-penetrating medical device (not shown) can include a needle assembly including a needle housing and a shaft of the needle having a sharp distal tip. The open proximal end 132 of cavity 270 provides a device-receiving space for receiving at least the shaft of the tissue-penetrating medical device.

Length $L_1$ represents the length to cover the shaft of a tissue-penetrating medical device, including the sharp distal tip to prevent accidental needle sticks. With respect to FIG. 2D, length $L_2$ refers to the length between the distal tip 272 of a cavity 270 to enclose a tissue-penetrating medical device and the distal tip 131 of cover 120. In one or more embodiments, the cavity 270 can be tubular or any other suitable shape. With respect to FIG. 2D, length $L_3$ refers to the length between the open proximal end 132 of cover 120 and the distal tip 131 of cover 120. When a cover 120 encloses a tissue-penetrating medical device and both are inserted into a magnetizer such that the distal tip 131 of cover 120 contacts the bottom of a cavity of a magnetizer, a desired section of the tissue-penetrating medical device of length $L_1$ will be exposed to the magnetic field to be magnetized.

The cavity 270 is sized and shaped to permit movement of the shaft of the tissue-penetrating medical device into and out of the device-receiving space. In one embodiment, the cavity 270 permits movement of the shaft of the tissue-penetrating medical device into the cavity 270 in a movement that is parallel to the longitudinal axis of the shaft of tissue-penetrating medical device. A metal portion of the tissue-penetrating medical device magnetizes when the tissue-penetrating medical device, with cover 120, is inserted into a separate magnetizer. In an alternate embodiment, a metal portion of the tissue-penetrating medical device magnetizes when the tissue-penetrating medical device, without cover 120, is inserted into a separate magnetizer. The magnetizer consists of a cavity with at least one opening through which the needle can be inserted. The cavity and the opening of the magnetizer are large enough to accommodate the tissue-penetrating medical device with its cover thus ensures the sterility and the integrity of the needle. The magnetizer can have openings on both ends to allow tissue-penetrating medical devices with various length and cover 110 or cover 120 of various lengths $L_3$ to be inserted to desired depth.

In one or more embodiments, as shown in FIG. 2C, length $L_1$ is less than length $L_3$. In one or more embodiments, as shown in FIG. 2C, length $L_2$ is less than length $L_3$. In one or more embodiments, as shown in FIG. 2C, length $L_3$ is about the sum of $L_1$ and length $L_2$. In one or more embodiments, as shown in FIG. 2D, length $L_1$ is approximately the same as length $L_3$.

The magnetizer further consists of magnetizing means around the cavity such as permanent magnets or electromagnets, or other magnetizing means. A section of the needle that is exposed to the magnetizing means is magnetized as the needle is removed from the magnetizer.

In one or more embodiments, the cover 110 and cover 120 can be transparent to allow the shaft and needle cannula of a tissue-penetrating medical device to be visible. In alternate embodiments, cover 110 and cover 120 can be opaque.

It is contemplated that in one or more embodiments, an outside surface of cover 110 or cover 120 may have a graduated injection depth gauge or marking to indicate the desired section of the needle to be magnetized when the needle and the needle cover are inserted into a magnetizer. In one or more embodiments, the graduated injection depth gauge may be printed onto an outer surface of the cover 110 or cover 120. In another embodiment, the graduated injection depth gauge may be engraved, etched, embossed, debossed by molding or formed onto an outer surface of the cover 110 or cover 120 to assist the practitioner in measuring the needle depth penetration. In one or more embodiments, the graduated injection depth gauge is scaled to correlate to a needle length.

In use, the user would insert the tissue-penetrating medical device with cover 110 or cover 120 into a magnetizer to magnetize a desired portion of the tissue-penetrating medical device. In one or more embodiments, lengths $L_1$, $L_2$ and/or $L_3$ may be varied depending on the length and/or gauge of the desired tissue-penetrating medical device. The cover 110 or cover 120 may have lines on it to show how far to insert cover for each needle length. The needle is inserted into a magnetizer with the cover on to contact the bottom of the magnetizer in order to obtain the desired length of magnetization without any additional action on the part of the user.

In one or more embodiments, the cover is sterile. In one or more embodiments, the cover is disposable. In one or more embodiments, the cover is plastic.

Figure 3A:
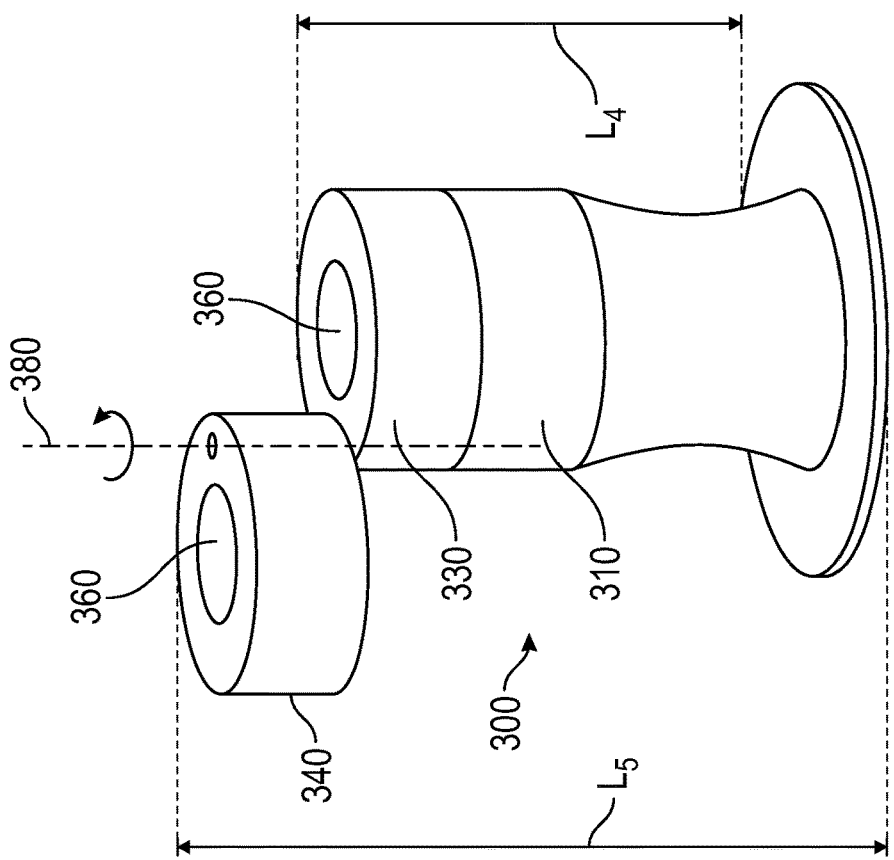
FIG. 3A shows a perspective view of yet another alternate embodiment of a needle magnetizer of the present disclosure.
Figure 3B:
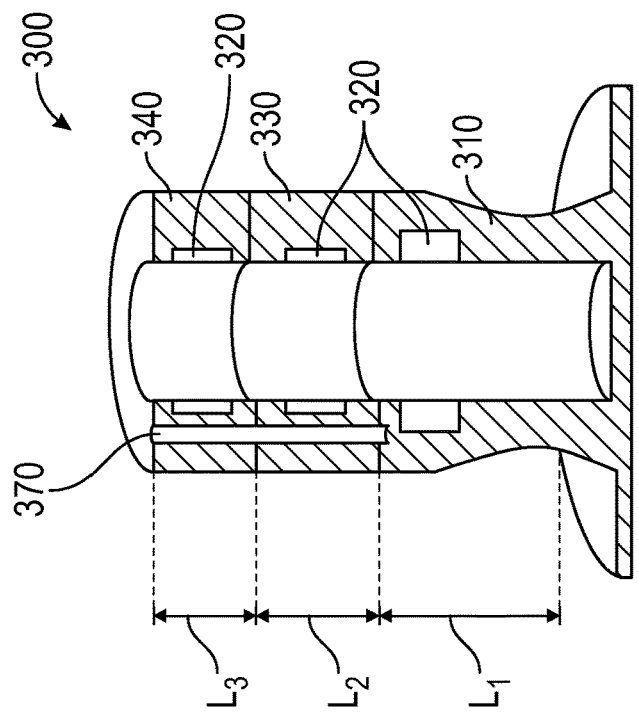
FIG. 3B illustrates a cross-section view of the needle magnetizer shown in FIG. 3A of the present disclosure.

A third aspect of the present disclosure, as shown in FIG. 3A and FIG. 3B, pertains to, a magnetizer 300 having a base segment 310 having one or more magnets 320, and one or more movable segments (330, 340) stacked in a vertical configuration on top of base segment 310. In one or more embodiments, movable segments (330, 340) may be in the form of a ring.

The base segment 310 and movable segments (330, 340) have a central cavity 360. The one or more of the movable segments (330, 340) pivot or move around a hinge 370 having vertical axis 380 not in contact with the cavity 360. In one or more embodiments, movable segments (330, 340) have one or more magnets 320. In one or more embodiments, magnetizer 300 as shown in FIG. 3A and FIG. 3B, can accommodate a needle cover of a uniform fixed length that can be used for needles of various different lengths. Thus, the insertion depth of the cover with respect to the bottom of the cavity 360 of the magnetizer 300 will be kept the same for needles of various different lengths. The number of the movable segments (330, 340) atop base segment 310 can be adjusted via moving the movable segments (330, 340) to correspond to the desired needle length enclosed in the cover. In one or more embodiments, when magnetizing a needle of the longest length, all movable segments (330, 340) atop base segment 310 will be used to form the magnetizing cavity 360. When magnetizing a needle of the shortest length, only the base segment 310 is used for magnetizing the needle, while the other movable segments (330, 340) are moved out of place. Therefore, movement of the movable segments adjusts the distance between the bottom of the magnetizing cavity 360 and the top of the magnetizer 300.

To adjust the length of the magnetizer to adjust to a tissue-penetrating medical device or cover of various lengths, one or more of the movable segments (330, 340) can be moved or rotated about the axis 380 so that the one or more of the movable segments (330, 340) is out of the way when tissue-penetrating medical devices, e.g. needles, with different lengths are inserted into cavity 360 of the magnetizer 300 to be magnetized.

Referring initially to FIG. 3A, the magnetizer 300 in accordance with an embodiment of the present disclosure has a cavity 360 formed in between a plurality of two or more movable segments (330, 340) and base segment 310 which are stacked and centered about a vertical axis 380. Each movable segment (330, 340) and base segment 310 has a center cavity 360 of sufficient size to receive a tissue-penetrating medical device, e.g. needles, of various lengths with a cover covering a portion or the entirety of the tissue-penetrating medical device. The cavity 360 of each movable segment (330, 340) and base segment 310 can be arranged and aligned in a circular array that is concentric with the axis 380 such that a tissue-penetrating medical device may be inserted into cavity 360. Cavity 360 is of sufficient size to receive a tissue-penetrating medical device, e.g. needles, of various lengths with a cover covering a portion or the entirety of the tissue-penetrating medical device. In one or more embodiment, base segment 310 can have an open proximal end and an open distal end. In one or more embodiment, base segment 310 can have an open proximal end and a closed distal end. In one or more embodiment, base segment 310 can have a closed proximal end and an open distal end. In one or more embodiments, the movable segments (330, 340) can be moved in rotational motion about axis 380 and may move or rotate in opposite directions or in the same direction. Each movable segment (330, 340) may be embedded with one or more magnets 320. In one or more embodiments, one or more magnet 320s is a permanent magnet. Certain of the above described characteristics of this embodiment of the invention are for purposes of example and can vary in other embodiments of the invention. In one or more embodiments, the number of segments, and their respective cavities, will depend on the dimensions including size, shape, height, length, etc. of the desired cover or tissue-penetrating medical device to be magnetized by the magnetizer. Each of the one or more movable segments (330, 340) and base segment 310 may be of various size, shape, length, height, diameter, radius, etc. depending on the desired tissue-penetrating medical device and/or cover to be inserted into the magnetizer comprised of one or more movable segments (330, 340) and base segment 310.

As shown in FIG. 3A, the movable segments (330, 340) are supported by a base segment 310, which may be in the form of an upright cylinder which extends upward. Each movable segment (330, 340) has a central extending cylindrical cavity to accommodate a tissue-penetrating medical device, e.g. needles, of various lengths with a cover covering a portion or the entirety of the tissue-penetrating medical device. Each segment can be in coaxial relationship with base segment 310. A hinge 370 couples each movable segment (330, 340) to support the base segment 310 while enabling movement or rotation of the each movable segment (330, 340).

In one or more embodiments each segment may be embedded with one or more magnet 320. In one or more embodiments, one or more magnets 320 can be a permanent magnet. In one or more embodiments, one or more segments may be moved or rotated about the vertical axis to vary the length of the cavity in which the tissue-penetrating medical device is placed. Therefore, by moving one or more segments about the vertical axis, the length of the cavity can be adjusted to a desired length. Therefore, the user can control the portion or length of the tissue-penetrating medical device to be magnetized. For example, as shown in FIG. 3B, base segment 310 has a length $L_1$, segment 330 has a length $L_2$ and segment 340 has a length $L_3$. Depending on the length of the cover or tissue-penetrating medical device to be magnetized, one or more segments may be moved about the vertical axis to vary the length of the cavity in which the tissue-penetrating medical device is placed. In one or more embodiments, movement may be rotational or translation. For example, if the desired length of the cover or tissue-penetrating medical device to be magnetized is $L_1$, then both segment 330 and segment 340 can be moved or rotated about the vertical axis to adjust the length of the cavity to $L_1$ in which the tissue-penetrating medical device is placed. For example, if the desired length of the cover or tissue-penetrating medical device to be magnetized is $L_4$, then segment 340 can be moved or rotated about the vertical axis to adjust the length of the cavity to $L_4$ (sum of $L_1$ and $L_2$) in which the tissue-penetrating medical device is placed. For example, if the desired length of the cover or tissue-penetrating medical device to be magnetized is $L_5$, then none of the segments (340, 350) are moved or rotated about the vertical axis. Instead segment 340 and segment 350 are aligned with base segment 310 to adjust the length of the cavity to $L_5$ (sum of $L_1$, $L_2$ and $L_3$) in which the tissue-penetrating medical device is placed. Therefore, the user can control the portion or length of the tissue-penetrating medical device to be magnetized.

In one or more embodiments, magnetizer 300 may be used with any cover 110 or 120 disclosed herein. In one or more embodiments, cover 110 or 120 may be a uniform length having one or more physical stop elements 150 disposed on the outer surface and is used with a tissue-penetrating medical device of variable lengths. In one or more embodiments, one or more physical stop elements 150 are molded onto the outer surface of cover 110 or 120. In one or more embodiments, the position of the physical stop elements 150 disposed on the outer surface of cover 110 or 120 correspond to different gauge or size of various tissue-penetrating medical devices to be used with cover 110 or 120. Therefore, the length or portion of the tissue-penetrating device that is magnetized when a user inserts cover 110 or 120 into a magnetizer 300 until the physical stop elements 150 disposed on the outer surface of cover 110 or 120 that corresponds to desired gauge or size of the tissue-penetrating medical device reaches the top of the magnetizer 300. Therefore, the length or portion of the tissue-penetrating device that is magnetized is dependent on the length of the tissue-penetrating medical device within the cover 110 or 120.

Magnetizer 300 can be used as a single use disposable item, or the magnetizer 300 may be reusable since the needle cover stays in place during the magnetization step. In other embodiments, the length $L_1$ of base segment 310, $L_2$ and $L_3$ of the respective segments (330, 340) and length $L_4$, $L_5$ of magnetizer 300 may be configured such that the entire or a desired portion of a shaft of the tissue-penetrating medical device can be magnetized. In other embodiments, the length $L_1$, $L_2$, $L_3$, $L_4$ and $L_5$ can be 10%, 20%, 30%, 40%, 50%, 60%, 70%, 80%, 90%, 100% or any intervening percentage of the length of the cover or tissue-penetrating medical device to be magnetized.

FIG. 3B shows a cross-sectional view of a magnetizer 300 having one or more embedded magnets 320 in the sidewall of the base segment and respective segments (330, 340) of the magnetizer 300. The one or more magnets 320 can be embedded in a slot. The one or more magnets 320 can be sized to be slidably mounted within a slot or held in place by friction fit, or the one or more magnets 320 can be attached with an adhesive or other suitable ways. Alternatively, one or more magnets 320 can be integrally molded in the sidewall of the base segment 310 and respective segments (330, 340) of the magnetizer 300. In one or more embodiments, the magnet may be a permanent magnet, electromagnet, or other magnetizing means.

In one or more embodiments, magnetizer 300 allows magnetic pole tip position to be changed with respect to the magnetizer cavity, particularly for the cases of where the magnetizer cavity only contains one opening. The top of the magnetizing means can be changed to be closer to the bottom of the cavity when magnetizing a needle with longer length.

Figure 4:
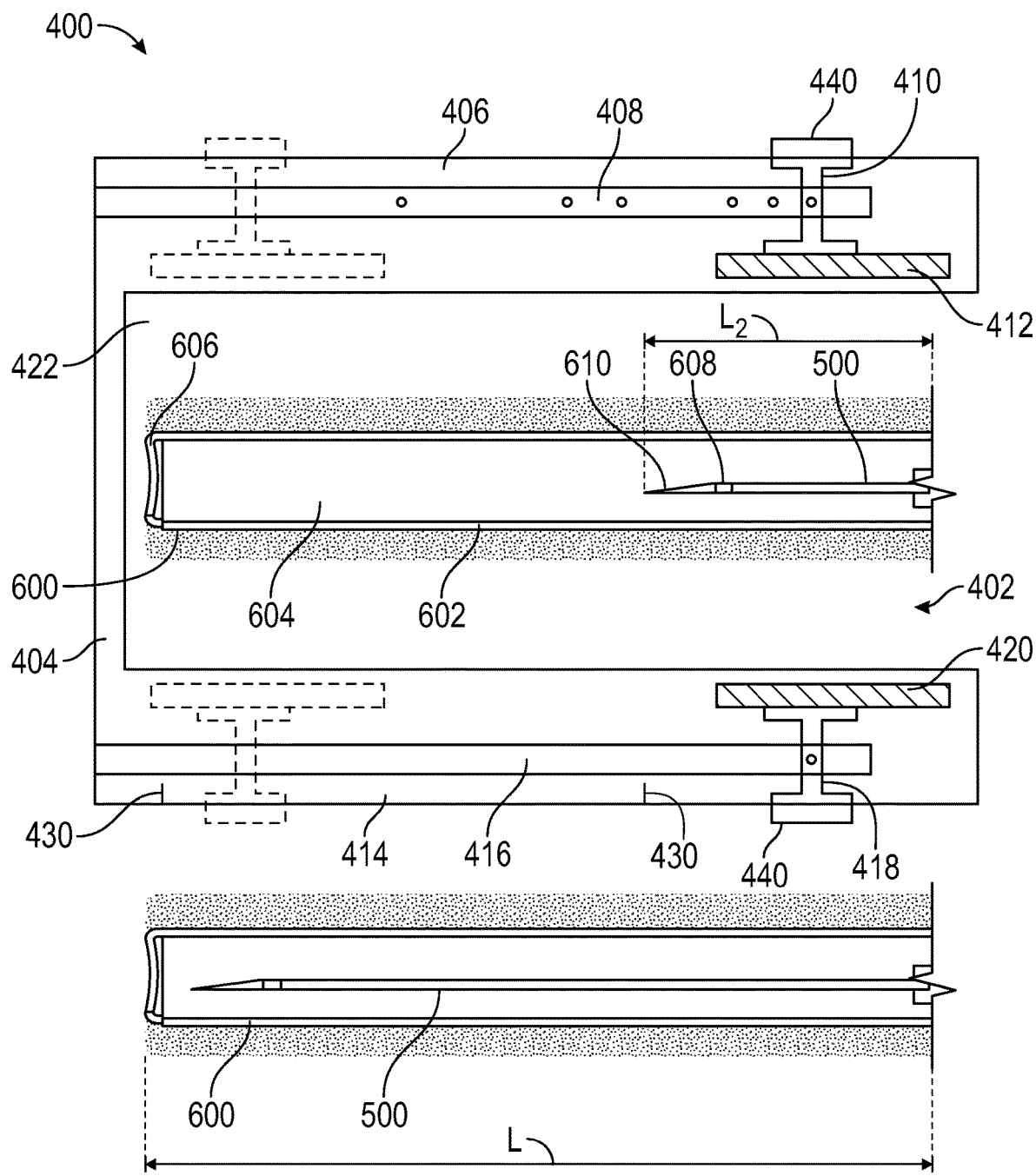
FIG. 4 illustrates a cross-section view of yet another alternate embodiment of a needle magnetizer of the present disclosure.

A fourth aspect of the present disclosure, as shown in FIG. 4, pertains to a magnetizer 400, having an open proximal end 402, a distal end 404, a first sidewall 406, a first sliding element 410 having one or more first magnets 412 slidably connected to the first sidewall 406, a second sidewall 414, a second sliding element 418 having one or more second magnets 420 slidably engaged to the second sidewall 414, a cavity 422 formed between the first sidewall 406, second sidewall 414 and distal end 404. The one or more first magnets are mounted on the first sliding element 410. The one or more second magnets 420 are mounted on the second sliding element 418. The first sliding element 410 and the second sliding element 418 can be moved in parallel to the axis of the cavity 422 to adjust the length of the magnetizer to magnetize a tissue-penetrating medical device 500 or cover 600 of various lengths that are inserted into cavity 422 of the magnetizer 400 allowing the adjustment of the distance between the bottom of the magnetizing cavity 422 and the top of the magnet (412/420). In one or more embodiments, first sidewall 406 can have a first slot 408, a first sliding element 410 having one or more first magnets 412, first sliding element 410 being slidably connected to the first slot 408, a second sidewall 414 having a second slot 416, a second sliding element 418 having one or more second magnets 420, second sliding element 418 being slidably engaged to the second slot 416, a cavity 422 formed between the first sidewall 406, second sidewall 414 and distal end 404.

One or more embodiments of the present disclosure relate to a needle magnetizer that is capable of accommodating tissue-penetrating medical device 500 or cover 600 of various lengths.

The cavity 422 is sized and shaped to permit movement of the tissue-penetrating medical device 500 or cover 600 into and out of cavity 422. In one embodiment, the cavity 422 permits movement of the tissue-penetrating medical device 500 or cover 600 into the cavity 422 in a movement that is parallel to the longitudinal axis of the shaft of tissue-penetrating medical device. The needle cannula magnetizes when the tissue-penetrating medical device 500 or cover 600 are placed into cavity 422 and subsequently first sliding element 410 and/or second sliding element 418 are moved in parallel to the axis of the cavity 422 to adjust the length of the magnetizer to magnetize a desired portion of the tissue-penetrating medical device 500 or cover 600 of various lengths that are inserted into cavity 422 of the magnetizer 400. The magnetizer consists of a cavity with at least one open proximal end 402 through which the tissue-penetrating medical device 500 or cover 600 can be inserted. The cavity 422 and the open proximal end 402 are large enough to accommodate the tissue-penetrating medical device 500 or cover 600 of various dimensions and lengths that are inserted into cavity 422 of the magnetizer 400 therefore ensuring the sterility and the integrity of the tissue-penetrating medical device. It is contemplated that in one or more embodiment, cavity 422 can have openings on both ends to allow needles with various length and needle cover length to be inserted to desired depth.

The first sliding element 410 and/or second sliding element 418 may be variably positioned along the length L of the cover 600 relative to the shaft of the tissue-penetrating medical device 500 to allow the user to control the portion or length of the tissue-penetrating medical device 500 to be magnetized. The magnetizer 400 can be used as a single use disposable item, or the magnetizer 400 may be reusable since the cover 600 stays in place during the magnetization step. Therefore, the user can control the portion or length of the tissue-penetrating medical device 500 to be magnetized. The slider can be slidably moved along the length of the cover 600 via the first slot 408 and the second slot 416. In other embodiments, the length of the first slot 408 and the second slot 416 may be equal to the length L of the cover 600 or tissue-penetrating medical device 500 such that the entire shaft of the tissue-penetrating medical device 500 can be magnetized. In other embodiments, the any desired portion (e.g. 10%, 20%, 30%, 40%, 50%, 60%, 70%, 80%, 90%, 100% or any increment therein) of the length L of the penetrating medical device 500 can be magnetized.

Magnet (412, 420) can be attached to the sliding elements (410, 418) with an adhesive or other suitable ways. Alternatively, the magnets (412, 420) could be integrally molded into sliding element (410, 418).

The magnet (412, 420) can be sized to be slidably mounted within the first sidewall (406) and/or second sidewall (414). In one or more embodiments, the magnet (412, 420) can be sized to be slidably mounted within the slot (408, 416).

In one or more embodiments, the magnet (412, 420) may be a permanent magnet, electro-magnets, or other magnetizing means.

It is contemplated that the first sidewall 406 and/or second sidewall 414 can have a graduated injection depth gauge or marking 430 to indicate the desired length or section of the needle to be magnetized when the needle and the needle cover are inserted into a magnetizer. In one or more embodiments, the graduated injection depth gauge may be printed onto an outer surface of the first sidewall 406 and/or second sidewall 414. In another embodiment, the graduated injection depth gauge may be engraved, etched, embossed, debossed by molding or formed onto an outer surface of the first sidewall 406 and/or second sidewall 414 to assist the practitioner in measuring the needle depth penetration. In one or more embodiments, the graduated injection depth gauge is scaled to correlate to a needle length.

In one or more embodiments, the first sliding element 410 and/or second sliding element 418 includes a contact surface having a profile for accommodating a practitioner's finger.

First sliding element 410 and/or second sliding element 418 may be configured to toggle in a parallel or perpendicular direction with respect to tissue-penetrating medical device 500 or cover 600.

Movement of the first sliding element 410 and/or second sliding element 418 from a forward end of the first sidewall 406 to the rearward end of the second sidewall 414 may be accomplished by exerting pressure on finger contact surface 440 of the first sliding element 410 and/or second sliding element 418.

FIG. 4 show a tissue-penetrating medical device 500, a cover 600 for magnetizing the shaft of the tissue-penetrating medical device 500. The cover 600 includes a sleeve member 602 having a hollow tubular body 604 having a distal end 606 and a proximal end (not shown) to form a protective closure over the shaft 608 of the tissue-penetrating medical device 500, the sleeve member 602 having a length L to cover the shaft 608 of the tissue-penetrating medical device 500, the shaft 608 having a length $L_2$ and a distal tip 610. An open end (not shown) of the hollow tubular body 604 provides a receiving space for receiving at least the shaft 608 of the tissue-penetrating medical device 500. In one or more embodiments, a single magnet can be utilized to magnetize the shaft 608, or more than two magnets can also be utilized.

In embodiments in which two magnets are utilized, the orientation of the magnetic fields of the two magnets can vary. One magnet can have north and south poles on axis with shaft of the tissue-penetrating medical device, while the second magnet can have north and south poles off-axis or perpendicular to the shaft of the tissue-penetrating medical device. Alternatively, the two magnets both can have north and south poles off axis with the shaft of the tissue-penetrating medical device, or the two magnets both can have north and south poles on axis with the shaft of the tissue-penetrating medical device.

Upon removal from magnetizer 400, the tissue-penetrating medical device 500 can now be used with a procedural guidance system that utilize magnetic sensors as a means of measuring and predicting needle tip location relative to the target anatomy.

In one or more embodiments, magnetizer 400 allows magnetic pole tip position to be changed with respect to the magnetizer cavity, particularly for the cases of where the magnetizer cavity only contains one opening. The top of the magnetizing means can be changed to be closer to the bottom of the cavity when magnetizing a needle with longer length.

In alternative embodiments, a needle cover is provided that has geometric dimensions that permit the needle cover to be placed inside existing needle magnetizing devices while the needle cover is covering the shaft of the needle. The distal end of the needle cover may be used to limit the depth of insertion by providing a stop to contact the bottom of the needle magnetizing device. Alternatively, a feature near the proximal portion of the needle cover can be provided on the cover to limit the depth of insertion by a stop on the proximal opening of the needle magnetizer.

The covers described herein can have a variety of properties. In one or more embodiments, the covers are formed from plastic. In one or more embodiments, the covers are sterile. In one or more embodiments, the covers are disposable. In other embodiments, the covers may be both sterile and disposable.

The tissue-penetrating medical device may be a needle, catheter, introducer needle, stylet, scalpel or guidewire. In one embodiment, the tissue-penetrating medical device is a needle, which when magnetized can be used with a procedural guidance system to locate and project the position of the needle during an invasive medical procedure. The tissue-penetrating medical device according to one or more embodiments is includes a magnetizable metallic material. In a specific embodiment, the magnetizable metallic material is stainless steel.

The covers described herein may also be incorporated into a vascular access device comprising a catheter, a catheter adapter subassembly, and a needle subassembly including an introducer needle, a needle hub connected to the proximal end of the introducer needle and a needle cover according to any of the embodiments described herein. The magnetizer of the present disclosure may also be used in conjunction with a vascular access device comprising a catheter, a catheter adapter subassembly, and a needle subassembly including an introducer needle.

Another aspect of the disclosure pertains to a method of magnetizing a tissue-penetrating medical device. Embodiments of the method include positioning a shaft of a tissue-penetrating medical device in a cover of the present disclosure including a device-receiving space, positioning the cover including tissue-penetrating medical device into a magnetizer and removing the cover with the tissue-penetrating medical device from the magnetizer to magnetize a desired portion of the tissue-penetrating medical device. Another embodiment of the method of the present disclosure includes positioning a shaft of a tissue-penetrating medical device in an available cover having a device-receiving space, positioning the cover with the tissue-penetrating medical device into a magnetizer of the present disclosure, and removing the cover with the tissue-penetrating medical device from the magnetizer of the present disclosure to magnetize a desired portion of the tissue-penetrating medical device.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A magnetizer for magnetizing a tissue-penetrating medical device comprising:
   an open proximal end;
   a distal end;
   a first sidewall;
   a first sliding element having one or more first magnets slidably connected to the first sidewall;
   a second sidewall;
   a cavity formed between the first sidewall, second sidewall and the distal end;
   the first sidewall having a first slot, the first sliding element being slidably connected to the first slot;
   the second sidewall having a second slot, a second sliding element having one or more second magnets, the second sliding element being slidably engaged to the second slot; and
   wherein movement of the first sliding element and the second sliding element is parallel to a direction of movement a user would employ to insert a tissue-penetrating medical device or a needle cover into the cavity to adjust a length of the magnetizer to magnetize the tissue-penetrating medical device or the needle cover of various lengths that are inserted into the cavity.

2. The magnetizer of claim 1, wherein the one or more first magnets are mounted on the first sliding element.

3. The magnetizer of claim 1, wherein the first sliding element includes a contact surface having a profile for accommodating a practitioner's finger.

4. The magnetizer of claim 1, wherein the second sliding element includes a contact surface having a profile for accommodating a practitioner's finger.

5. The magnetizer of claim 1, wherein the cavity is configured to accommodate the tissue-penetrating medical device.

6. The magnetizer of claim 5, wherein the tissue-penetrating medical device is a needle assembly, a stylet, catheter, introducer needle, scalpel or guidewire.

7. The magnetizer of claim 6, wherein the tissue-penetrating medical device includes a needle assembly including a needle having a shaft, and when the shaft is magnetized, the tissue-penetrating medical device is configured for use in a procedural guidance system to locate and project a position of the shaft during an invasive medical procedure.

8. The magnetizer of claim 1, wherein the cavity is configured to accommodate the needle cover.

9. The magnetizer of claim 1, wherein the one or more first magnets comprises a fixed permanent magnet.

10. The magnetizer of claim 1, wherein the first sliding element is moveable along the first sidewall.

11. The magnetizer of claim 1, wherein the second sliding element is moveable along the second sidewall.

* * * * *

UNITED STATES PATENT AND TRADEMARK OFFICE
CERTIFICATE OF CORRECTION

PATENT NO. : 11,413,430 B2
APPLICATION NO. : 16/943162
DATED : August 16, 2022
INVENTOR(S) : Yiping Ma et al.

It is certified that error appears in the above-identified patent and that said Letters Patent is hereby corrected as shown below:

In the Specification

• Column 9, Line 59, after "tip", replace "172" with "272".

Signed and Sealed this
Eighteenth Day of October, 2022

Katherine Kelly Vidal
*Director of the United States Patent and Trademark Office*